US007247457B2

(12) United States Patent
Nix et al.

(10) Patent No.: US 7,247,457 B2
(45) Date of Patent: Jul. 24, 2007

(54) DETECTION AND IDENTIFICATION OF ENTEROVIRUSES BY SEMI-NESTED AMPLIFICATION OF THE ENTEROVIRUS VP1 PROTEIN

(75) Inventors: William Allan Nix, Bethlehem, GA (US); M. Steven Oberste, Lilburn, GA (US)

(73) Assignee: United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 11/115,860

(22) Filed: Apr. 26, 2005

(65) Prior Publication Data

US 2006/0240407 A1    Oct. 26, 2006

(51) Int. Cl.
C12P 19/34 (2006.01)
C12Q 1/70 (2006.01)
(52) U.S. Cl. .......................................... 435/91.2; 435/5
(58) Field of Classification Search ............ None
See application file for complete search history.

(56) References Cited

U.S. PATENT DOCUMENTS

| | | | | | |
|---|---|---|---|---|---|
| 4,719,177 | A | * | 1/1988 | Baltimore et al. | 435/91.51 |
| 6,168,917 | B1 | * | 1/2001 | Kilpatrick | 435/5 |
| 6,200,576 | B1 | * | 3/2001 | Hwong et al. | 424/216.1 |
| 6,255,458 | B1 | * | 7/2001 | Lonberg et al. | 530/388.15 |
| 6,258,537 | B1 | * | 7/2001 | Keinath et al. | 435/6 |
| 6,365,345 | B1 | * | 4/2002 | Brysch et al. | 435/6 |
| 6,538,173 | B2 | * | 3/2003 | Heber-Katz | 800/8 |
| 6,818,397 | B1 | | 11/2004 | Lee et al. | |
| 6,846,621 | B1 | | 1/2005 | Oberste et al. | |
| 2005/0048475 | A1 | | 3/2005 | Paul, III et al. | |

OTHER PUBLICATIONS

Bailly et al., Genetic Diversity of Echovirus 30 During a Meningitis Outbreak, Demonstrated by Direct Molecular Typing From Cerebrospinal Fluid, 2002, J. Med. Virology 68: 558-567.*
Buck et al., Design Strategies and Performance of Custom DNA Sequencing Primers, 1999, BioTechniques, 27: 528-536.*
Brown et al., Complete Genomic Sequnecing Shows that Polioviruses and Members of Human Enterovirus Species C are Closely Related in the Noncaspid Coding Region, Aug. 2003, J. Med. Virology, 8973-8984.*
Caro et al., "Molecular Strategy for 'Serotyping' of Human Enteroviruses," *J. Gen. Virol.* 82:79-91 (2001).
Casas et al., "Molecular Characterization of Human Enteroviruses in Clinical Samples: Comparison Between VP2, VP1, and RNA Polymerase Regions Using RT Nested PCR Assays and Direct Sequence of Products," *J. Med. Virol.* 65:138-148 (2001).
Lovchik et al., "Novel Enterovirus Associated with Hospitalizations for Asthma in Children," Clinical Virology Symposium, Apr. 27, 2004 (abstract).
Nix et al., "Rapid Identification of Enteroviruses in Clinical Specimens by VP1 Seminested PCR and Amplicon Sequencing," Clinical Virology Symposium, Apr. 27, 2004 (abstract).
Nix et al., "Failure to Defect Enterovirus in the Spinal Cord of ALS Patients Using a Sensitive RT-PCR Method," *Neurology* 62:1372-1377 (2004).
Norder et al., "Homotypic Echoviruses Share Aminoterminal VP1 Sequence Homology Applicable for Typing," *J. Med. Virol.* 63:35-44 (2001) (abstract).
Oberste et al., "Comparison of Classic and Molecular Approaches for the Identification of Untypeable Enteroviruses," *J. Clin. Microbiol.* 38:1170-1174 (2000).
Oberste et al., "Improved Molecular Identification of Enteroviruses by RT-PCR and Amplicon Sequencing," *J. Clin. Virol.* 26:375-377 (2003).
Rose et al., "Consensus-Degenerate Hybrid Oligonucleotide Primers for Amplification of Distantly Related Sequences," *Nucleic Acids Res.* 26:1628-1635 (1998).
Rose et al., "CODEHOP (COnsensus-DEgenerate Hybrid Oligonucleotide Primer) PCR Primer Design," *Nucleic Acids Res.* 31:3763-3766 (2003).
Thoelen et al., "Molecular Typing and Epidemiology of Enteroviruses Identified From an Outbreak of Aseptic Meningitis in Belgium During the Summer of 2000," *J. Med. Virol.* 70:420-429 (2003).

\* cited by examiner

*Primary Examiner*—Kenneth R. Horlick
*Assistant Examiner*—Mark Staples
(74) *Attorney, Agent, or Firm*—Klarquist Sparkman, LLP

(57) ABSTRACT

Disclosed are methods of using enterovirus-specific primers for the detection and identification of enterovirus infection. Also provided are isolated nucleic acid molecules and kits useful for detection and diagnostic testing of enterovirus infection in a subject.

11 Claims, 4 Drawing Sheets

FIG. 1A

SEQUENCE LISTING

```
<160> NUMBER OF SEQ ID NOS: 32

<210> SEQ ID NO 1
<211> LENGTH: 8
<212> TYPE: DNA
<213> ORGANISM: Artificial Sequence
<220> FEATURE:
<223> OTHER INFORMATION: Oligonucleotide cDNA primer.

<400> SEQUENCE: 1 gtytgcca                                                             8

<210> SEQ ID NO 2
<211> LENGTH: 8
```

```
<212> TYPE: DNA
<213> ORGANISM: Artificial Sequence
<220> FEATURE:
<223> OTHER INFORMATION: Oligonucleotide cDNA primer.

<400> SEQUENCE: 2 gaytgcca                                                                    8

<210> SEQ ID NO 3
<211> LENGTH: 8
<212> TYPE: DNA
<213> ORGANISM: Artificial Sequence
<220> FEATURE:
<223> OTHER INFORMATION: Oligonucleotide cDNA primer.

<400> SEQUENCE: 3 ccrtcrta                                                                    8

<210> SEQ ID NO 4
<211> LENGTH: 9
<212> TYPE: DNA
<213> ORGANISM: Artificial Sequence
<220> FEATURE:
<223> OTHER INFORMATION: Oligonucleotide cDNA primer.

<400> SEQUENCE: 4 rctytgcca                                                                   9

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (15)..(15)
<223> OTHER INFORMATION: n = inosine

<400> SEQUENCE: 5
gcnatgytng gnacncayrt                                                      20

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (2)..(2)
<223> OTHER INFORMATION: n = inosine
<220> FEATURE:
<221> NAME/KEY: misc_feature
<222> LOCATION: (5)..(5)
<223> OTHER INFORMATION: n = inosine
<220> FEATURE:
<221> NAME/KEY: misc_feature
<222> LOCATION: (8)..(8)
```

<223> OTHER INFORMATION: n = inosine
<220> FEATURE:
<221> NAME/KEY: misc_feature
<222> LOCATION: (11)..(11)
<223> OTHER INFORMATION: n = inosine

<400> SEQUENCE: 6
cnccnggngg nayrwacat                                                19

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (15)..(15)
<223> OTHER INFORMATION: n = inosine
<220> FEATURE:
<221> NAME/KEY: misc_feature
<222> LOCATION: (18)..(18)
<223> OTHER INFORMATION: n = g, a, t, or c

<400> SEQUENCE: 7
acngcngyng aracnggnca                                               20

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (15)..(15)
<223> OTHER INFORMATION: n = inosine
<220> FEATURE:
<221> NAME/KEY: misc_feature
<222> LOCATION: (18)..(18)
<223> OTHER INFORMATION: n = g, a, t, or c

<400> SEQUENCE: 8
acngcngtng aracnggng                                                19

<210> SEQ ID NO 9
<211> LENGTH: 20
<212> TYPE: DNA
<213> ORGANISM: Artificial Sequence

```
<220> FEATURE:
<223> OTHER INFORMATION: Oligonucleotide amplification primer.
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (15)..(15)
<223> OTHER INFORMATION: n = inosine
<220> FEATURE:
<221> NAME/KEY: misc_feature
<222> LOCATION: (18)..(18)
<223> OTHER INFORMATION: n = g, a, t, or c

<400> SEQUENCE: 9
cargcngcng aracnggngc                                              20

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (2)..(2)
<223> OTHER INFORMATION: n = inosine
<220> FEATURE:
<221> NAME/KEY: misc_feature
<222> LOCATION: (5)..(5)
<223> OTHER INFORMATION: n = inosine
<220> FEATURE:
<221> NAME/KEY: misc_feature
<222> LOCATION: (8)..(8)
<223> OTHER INFORMATION: n = inosine
<220> FEATURE:
<221> NAME/KEY: misc_feature
<222> LOCATION: (14)..(14)
<223> OTHER INFORMATION: n = g, a, t, or c

<400> SEQUENCE: 10
mngcngynga racngg                                                  16

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (18)..(18)
<223> OTHER INFORMATION: n = g, a, t, or c
<220> FEATURE:
<221> NAME/KEY: misc_feature
<222> LOCATION: (24)..(24)
<223> OTHER INFORMATION: n = g, a, t, or c

<400> SEQUENCE: 11
ccagcactga cagcagynga rayngg                                       26

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide amplification primer.
<220> FEATURE:
```

```
<221> NAME/KEY: misc_feature
<222> LOCATION: (16)..(16)
<223> OTHER INFORMATION: n = g, a, t, or c
<220> FEATURE:
<221> NAME/KEY: misc_feature
<222> LOCATION: (19)..(19)
<223> OTHER INFORMATION: n = g, a, t, or c

<400> SEQUENCE: 12
tactggacca cctggnggna yrwacat                                          27

<210> SEQ ID NO 13
<211> LENGTH: 32
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (24)..(24)
<223> OTHER INFORMATION: n = inosine
<220> FEATURE:
<221> NAME/KEY: misc_feature
<222> LOCATION: (30)..(30)
<223> OTHER INFORMATION: n = g, a, t, or c

<400> SEQUENCE: 13
gaagtaccag cactgacagc agyngarayn gg                                    32

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (24)..(24)
<223> OTHER INFORMATION: n = inosine
<220> FEATURE:
<221> NAME/KEY: misc_feature
<222> LOCATION: (27)..(27)
<223> OTHER INFORMATION: n = inosine

<400> SEQUENCE: 14
ctgtttggta ctggaccacc tggnggnayr wacat                                 35

<210> SEQ ID NO 15
<211> LENGTH: 15
<212> TYPE: DNA
<213> ORGANISM: Artificial Sequence
<220> FEATURE:
<223> OTHER INFORMATION: Oligonucleotide amplification primer.

<400> SEQUENCE: 15
ccagcactga cagca                                                       15

<210> SEQ ID NO 16
<211> LENGTH: 15
<212> TYPE: DNA
<213> ORGANISM: Artificial Sequence
<220> FEATURE:
<223> OTHER INFORMATION: Oligonucleotide amplification primer.

<400> SEQUENCE: 16
tactggacca cctgg                                                       15

<210> SEQ ID NO 17
<211> LENGTH: 28
```

```
<212> TYPE: DNA
<213> ORGANISM: Artificial Sequence
<220> FEATURE:
<223> OTHER INFORMATION: Oligonucleotide amplification primer.

<400> SEQUENCE: 17
aattaaccct cactaaaggg agaagata                                28

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide amplification primer.
<220> FEATURE:
<221> NAME/KEY: misc_feature
<222> LOCATION: (16)..(16)
<223> OTHER INFORMATION: n = g, a, t, or c

<400> SEQUENCE: 18
gtcagctggg tttatnccrt a                                      21

<210> SEQ ID NO 19
<211> LENGTH: 7
<212> TYPE: PRT
<213> ORGANISM: Artificial Sequence
<220> FEATURE:
<223> OTHER INFORMATION: Conserved enterovirus amino acid motif used
      in primer design.
<220> FEATURE:
<221> NAME/KEY: MISC_FEATURE
<222> LOCATION: (7)..(7)
<223

```
<222> LOCATION: (3)..(3)
<223> OTHER INFORMATION: Xaa = Ala or Val

<400> SEQUENCE: 21

Thr Ala Xaa Glu Thr Gly His
1               5

<210> SEQ ID NO 22
<211> LENGTH: 7
<212> TYPE: PRT
<213> ORGANISM: Artificial Sequence
<220> FEATURE:
<223> OTHER INFORMATION: Conserved enterovirus amino acid motif used
      in primer design.
<220> FEATURE:
<221> NAME/KEY: MISC_FEATURE
<222> LOCATION: (7)..(7)
<223>

```
<400> SEQUENCE: 25

Pro Ala Leu Thr Ala Xaa Glu Xaa Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Conserved enterovirus amino acid motif used
      in primer design.
<220> FEATURE:
<221> NAME/KEY: MISC_FEATURE
<222> LOCATION: (2)..(2)
<223> OTHER INFORMATION: Xaa = Phe or Tyr
<220> FEATURE:
<221> NAME/KEY: MISC_FEATURE
<222> LOCATION: (3)..(3)
<223> OTHER INFORMATION: Xaa = Ile or Val

<400> SEQUENCE: 26

Met Xaa Xaa Pro Pro Gly Gly Pro Val
1               5

<210> SEQ ID NO 27
<211> LENGTH: 11
<212> TYPE: PRT
<213> ORGANISM: Artificial Sequence
<220> FEATURE:
<223> OTHER INFORMATION: Conserved enterovirus amino acid motif used
      in primer design.
<220> FEATURE:
<221> NAME/KEY: MISC_FEATURE
<222> LOCATION: (8)..(8)
<223> OTHER INFORMATION: Xaa = Ala or Val
<220> FEATURE:
<221> NAME/KEY: MISC_FEATURE
<222> LOCATION: (10)..(10)
<223> OTHER INFORMATION: Xaa = Ile or Thr

<400> SEQUENCE: 27

Glu Val Pro Ala Leu Thr Ala Xaa Glu Xaa Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Conserved enterovirus amino acid motif used
      in primer design.
<220> FEATURE:
<221> NAME/KEY: MISC_FEATURE
<222> LOCATION: (4)..(4)
<223> OTHER INFORMATION: Xaa = Phe or Tyr
<220> FEATURE:
<221> NAME/KEY: MISC_FEATURE
<222> LOCATION: (5)..(5)
<223> OTHER INFORMATION: Xaa = Ile or Val

<400> SEQUENCE: 28

Val Trp Met Xaa Xaa Pro Pro Gly Gly Pro Val
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Conserved enterovirus amino acid motif used
      in primer design.
```

```
<400> SEQUENCE: 29

Pro Ala Leu Thr Ala
1               5

<210> SEQ ID NO 30
<211> LENGTH: 5
<212> TYPE: PRT
<213> ORGANISM: Artificial Sequence
<220> FEATURE:
<223> OTHER INFORMATION: Conserved enterovirus amino acid motif used
      in primer design.

<400> SEQUENCE: 30

Pro Gly Gly Pro Val
1               5

<210> SEQ ID NO 31
<211> LENGTH: 6
<212> TYPE: PRT
<213> ORGANISM: Artificial Sequence
<220> FEATURE:
<223> OTHER INFORMATION: Conserved enterovirus amino acid motif used
      in primer design.

<400> SEQUENCE: 31

Arg Tyr Tyr Thr His Trp
1               5

<210> SEQ ID NO 32
<211> LENGTH: 7
<212> TYPE: PRT
<213> ORGANISM: Artificial Sequence
<220> FEATURE:
<223> OTHER INFORMATION: Conserved enterovirus amino acid motif used
      in primer design.

<400> SEQUENCE: 32

Tyr Gly Ile Asn Pro Ala Asp
1               5
```

DETECTION AND IDENTIFICATION OF ENTEROVIRUSES BY SEMI-NESTED AMPLIFICATION OF THE ENTEROVIRUS VP1 PROTEIN

FIELD OF THE DISCLOSURE

This disclosure relates to methods of amplifying enterovirus (EV) nucleic acid molecules and to methods of detecting an EV infection in a subject.

BACKGROUND

Enteroviruses (EVs) (genus *Enterovirus*, family Picornaviridae) constitute a broad range of pathogens etiologically responsible for a wide range of diseases in both humans and in other animals. Enteroviruses are small RNA viruses that contain positive, single stranded RNA as the genome. Five groups are found within the enteroviruses: coxsackievirus A, coxsackievirus B, echovirus, poliovirus, and the numbered enteroviruses. Most EV infections are asymptomatic or result in only mild symptoms, such as non-specific febrile illness or mild upper respiratory symptoms (for example, the common cold). However, enteroviruses can also cause a wide variety of other clinical illnesses, including acute hemorrhagic conjunctivitis, aseptic meningitis, undifferentiated rash, acute flaccid paralysis, myocarditis, and neonatal sepsis-like disease.

Molecular diagnostic tests to detect EV in clinical specimens usually target highly conserved sites in the 5' non-translated region (5'-NTR), allowing detection of all members of the genus (Romero, J. R., *Arch. Path. & Lab. Med.* 123:1161-69, 1999). These tests are genus-specific and provide an EV-positive or EV-negative result but cannot be used to identify the serotype.

Molecular diagnostic tests that target the EV VP1 capsid gene, which correlates with serotype determined by antigenic methods (Oberste et al., *J. Virol.* 73:1941-48, 1999), can provide both virus detection and identification (Oberste et al., *J. Clin. Microbiol.* 38:1170-74, 2000 and Oberste et al., *J. Clin. Virol.* 26:375-77, 2003). However, the identification of serotype, particularly from clinical specimens, is problematic because the virus titer is very low in original specimens. As a result, non-specific amplification can outcompete virus-specific amplification. Additionally, highly degenerate, inosine-containing primers used in diagnostic tests to broaden specificity to include all serotypes (Casas et al., *J. Med. Virol.* 65:138-48, 2001) often result in non-specific amplification of host cell nucleic acids that obscure the virus-specific product (Rose et al., *Nucl. Acids. Res.* 26:1628-35, 1998). To overcome these limitations additional molecular diagnostic methods are needed.

SUMMARY OF THE DISCLOSURE

Methods that allow the detection and identification of EVs have been developed and are described herein. The methods include detecting the presence of an EV amplicon containing at least a portion of the EV VP1 encoding sequence and sequencing the EV amplicon, and permit the diagnosis and identification of the EV serotype involved in a enterovirus infection. The provided methods are useful in detecting the presence of an EV in a sample and/or diagnosing an EV infection in a subject.

This disclosure also provides isolated nucleic acid molecules, which nucleic acid molecules have a nucleotide sequence as set forth in SEQ ID NO: 11, SEQ ID NO: 12, SEQ ID NO: 13, or SEQ ID NO: 14. In disclosed examples, these nucleic acid molecules are EV-specific primers for the detection and identification of EV infection. Also described herein are kits that include one or more nucleic acid cDNA primers that hybridize to an EV VP1 encoding sequence, a first PCR nucleic acid primer pair, wherein the first forward PCR primer hybridizes to an EV VP3 encoding sequence and the first reverse PCR primer hybridizes to an EV VP1 sequence, and a second PCR nucleic acid primer pair, wherein both the second forward and reverse PCR primers hybridize to an EV VP1 encoding sequence.

The foregoing and other features and advantages will become more apparent from the following detailed description of several embodiments, which proceeds with reference to the accompanying figures.

BRIEF DESCRIPTION OF THE FIGURES

FIGS. 1A-1B illustrate the location of the primers used in the COnsensus DEgenerate Hybrid Oligonucleotide Primer (CODEHOP) VP1 reverse transcription/semi-nested polymerase chain reaction (RT-snPCR). FIG. 1A is a similarity plot of the aligned capsid amino acid sequences of 64 enterovirus prototype strains. Sequence identity scores were calculated within each six residue window and the window progressively moved across the alignment in one-residue increments, with the identity score plotted versus position at the center of the window. Positions of the four mature EV capsid proteins, VP4, VP2, VP3, and VP1 are shown at the top. Orientation and approximate position of the cDNA primers (open arrowheads) and PCR primers (filled arrowheads) are shown directly above the plot. FIG. 1B illustrates the amino acid motifs used in primer design and the steps in the CODEHOP VP1 RT-snPCR assay. Consensus amino acid motifs are shown. Asterisks indicate that the residue directly above the asterisk is present at that position in at least 90% of EV prototype strains. When only a single residue is shown, it is present in all prototype strains. Primer sequences are shown directly below the amino acid motif sequences. Primers AN32, AN33, AN34, and AN35 (SEQ ID NOs: 1-4, respectively); primer 224 (SEQ ID NO: 5); primer 222 (SEQ ID NO: 6); primer AN89 (SEQ ID NO: 11); and primer AN88 (SEQ ID NO: 12). IUB ambiguity codes: R=A or G; Y=C or T; W=A or T; N=A, C, G, or T; M=A or C; I=Inosine.

FIG. 1A illustrates the amplification of RNA extracted from 10-fold serial dilutions of an EV68 virus stock. FIG. 1B illustrates the amplification of 10-fold serial dilutions of VP3-VP1 sRNA. FIG. 1C shows a comparison of VP1 RT-snPCR (top) with 5'-NTR RT-snPCR (bottom) using 10-fold serial dilutions.

SEQUENCE LISTING

Figure 2:
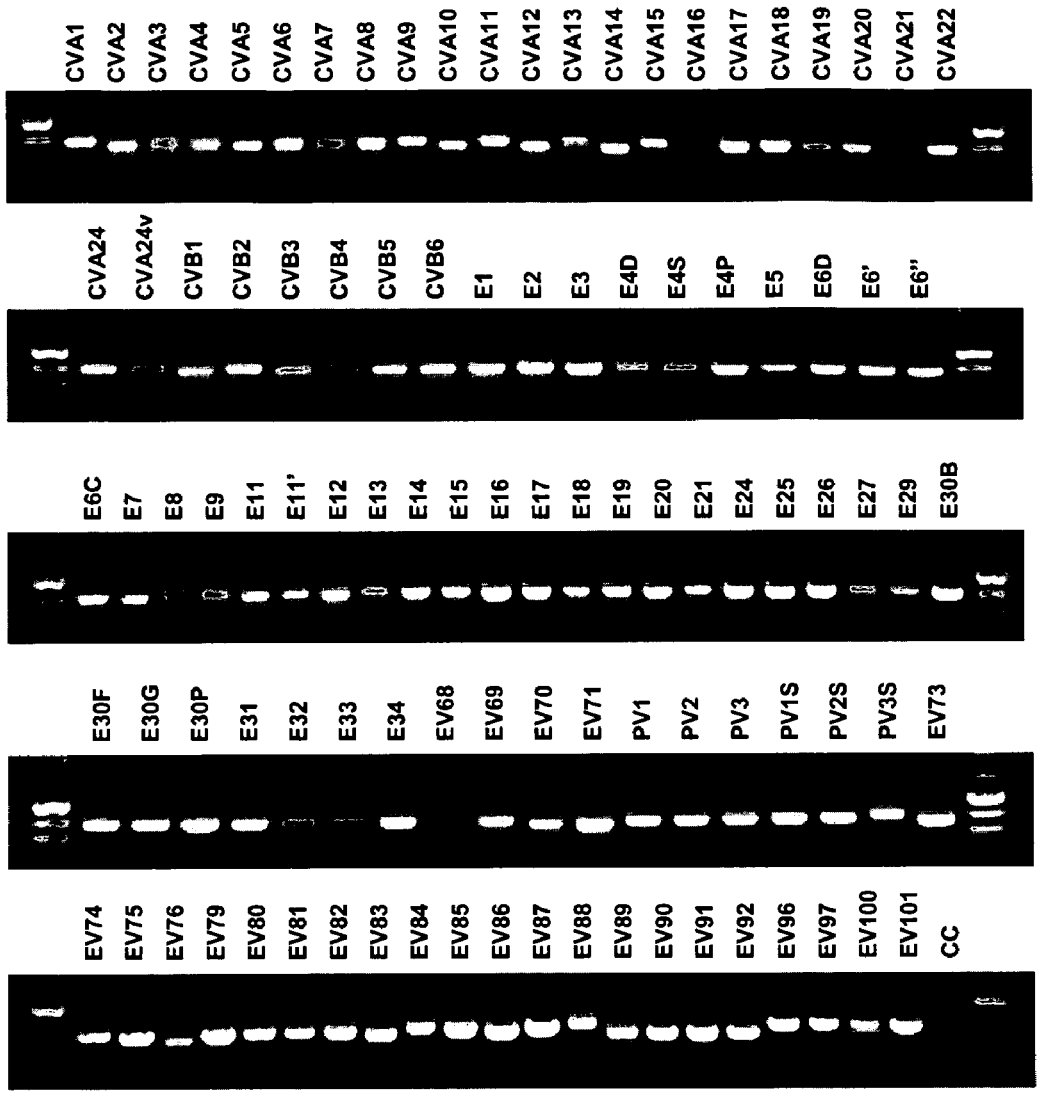
FIG. 2 illustrates the amplification of 101 EV reference strains by VP1 RT-snPCR. Primers AN32, AN33, AN34, and AN35 (SEQ ID NOs: 1-4, respectively) were used for cDNA synthesis. Primers 224 (SEQ ID NO: 5) and 222 (SEQ ID NO: 6) were used in the first PCR, and primers AN89 (SEQ ID NO: 11) and AN88 (SEQ ID NO: 12) were used in the second PCR. The strains tested were CVA1-Tomkins, CVA2-Fleetwood, CVA3-Olson, CVA4-High Point, CVA5-Swartz, CVA6-Gdula, CVA7-Parker, CVA8-Donovan, CVA9-Griggs, CVA10-Kowalik, CVA11-Belgium-1, CVA12-Texas-12, CVA13-Flores, CVA14-G-14, CVA15-G-9, CVA16-G-10, CVA17-G12, CVA18, G-13, CVA19-NIH-8663, CVA20-1H-35, CVA21-Coe, CVA22-Chulman, CVA24-Joseph, CVA24-EH24-70 (CVA24v), CVB1-Japan, CVB2-Ohio-1, CVB3-Nancy, CVB4-JVB, CVB5-Faulkner, CVB6-Schmitt, E1-Farouk, E2-Cornelis, E3-Morrisey, E4-Dutoit (E4D), E4-Shropshire (E4S), E4-Pesacek (E4P), E5-Noyce, E6-D'Amori (E6D), E6-Cox (E6'), E6-Burgess, (E6"), E6-Charles (E6C), E7-Wallace, E8-Bryson, E9-Hill, E11-Gregory, E11-Silva (E11'), E12-Travis, E13-Del Carmen, E14-Tow, E15-CH96-51, E16-Harrington, E17-CHHE-29, E18-Metcalf, E19-Burke, E20-JV-1, E21-Farina, E24-DeCamp, E25-JV-4, E26-Coronel, E27-Bacon, E29-JV-10, E30-Bastianni (E30B), E30-Frater (E30F), E30-Giles (E30G), E30-PR-17 (E30P), E31-Caldwell, E32-PR-10, E33-Toluca-3, E34-DN-19, EV68-Fermon, EV69-Toluca-1, EV70-J670/71, EV71-BrCr, PV1-Mahoney, PV2-Lansing, PV3-Leon, PV1-Sabin, PV2-Sabin, PV3, Sabin, EV73-CA55-1988, EV74-10213, EV75-10219, EV76-10226, EV79-10244, EV80-10246, EV81-10248, EV82-10249, EV83-10251, EV84-10603, EV85-10353, EV86-10354, EV87-10396, EV88-10398, EV89-10359, EV90-10399, EV91-10406, EV92-10408, EV96-10358, EV97-10355, EV100-10500, and EV101-10361. Reference strains for EV77-78 and EV93-95 were not included. Other numbers are missing due to reclassification (for example, CVA23 is a variant of E9; E10 is reovirus 1, genus *Orthoreovirus*, family Reoviridae; E28 is human rhinovirus 1A, genus *Rhinovirus*, family Picornaviridae; EV72 is human hepatitis A virus, genus *Hepatovirus*, family Picornaviridae). Also, E8 is a variant of E1 and E34 is a variant of CVA24. For each reaction, 10 µl of each semi-nested PCR2 product was analyzed by electrophoresis on a 1.5% agarose gel, containing 0.5 micrograms ethidium bromide per milliliter. Lanes at the ends of each row are DNA size markers. The negative control reaction, using uninfected cell culture RNA (CC), is shown in the bottom row.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-4 show the nucleic acid sequence of several EV-specific reverse oligonucleotide primers for cDNA synthesis.

SEQ ID NOs: 5-14 show the nucleic acid sequence of several EV-specific oligonucleotide primers (forward and reverse) for DNA amplification.

SEQ ID NO: 15 shows the nucleic acid sequence of the non-degenerate "clamp" portion of primer AN89.

SEQ ID NO: 16 shows the nucleic acid sequence of the non-degenerate "clamp" portion of primer AN88.

SEQ ID NOs: 17 and 18 show the nucleic acid sequence of a pair of EV-specific oligonucleotide primers (sense and antisense) for generation of a synthetic RNA standard.

SEQ ID NOs: 19-32 show the amino acid sequence of several conserved amino acid sequences from which EV-specific oligonucleotide primers were derived by back-translation.

DETAILED DESCRIPTION

I. Abbreviations

| | |
|---|---|
| BAL: | bronchoalveolar lavage |
| ° C.: | degrees Celsius |
| cDNA: | complementary DNA |
| CSF: | cerebrospinal fluid |
| DTT: | dithiothreitol |
| ES: | eye (conjunctival) swab |
| EV: | enterovirus |
| g: | gram |
| min: | minute(s) |
| ml: | milliliter |
| NPS: | nasopharyngeal swab |
| PCR: | polymerase chain reaction |
| RS: | rectal swab |
| RT-snPCR: | reverse transcription semi-nested polymerase chain reaction |
| µg: | microgram(s) |
| µl: | microliter(s) |
| s: | second(s) |

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of this disclosure, the following explanations of specific terms are provided:

Amplification of or amplifying a nucleic acid sequence: Increasing the amount of (number of copies of) a nucleic acid sequence, wherein the increased sequence is the same as or complementary to the existing nucleic acid template. The resulting amplification products are called "amplicons." An example of amplification is the polymerase chain reaction (PCR). Other examples of amplification techniques include reverse-transcription PCR (RT-PCR), semi-nested RT-PCR (RT-snPCR), strand displacement amplification (see U.S. Pat. No. 5,744,311), transcription-free isothermal amplification (see U.S. Pat. No. 6,033,881), repair chain reaction amplification (see WO 90/01069), ligase chain reaction amplification (see EP-A-320 308), gap filling ligase chain reaction amplification (see U.S. Pat. No. 5,427,930), coupled ligase detection and PCR (see U.S. Pat. No. 6,027,889), and NASBA™ RNA transcription-free amplification (see U.S. Pat. No. 6,025,134).

The products of amplification may be characterized by, for instance, electrophoresis, restriction endonuclease cleavage patterns, hybridization, ligation, and/or nucleic acid sequencing, using standard techniques.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antisense and sense: Double-stranded DNA (dsDNA) has two strands, a 5' to 3' strand, referred to as the plus strand, and a 3' to 5' strand, referred to as the minus strand. Because RNA polymerase adds nucleic acids in a 5' to 3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA.

Detect: To determine the existence or presence of something. For example, to determine whether an enterovirus or an EV nucleic acid sequence is present in a sample (such as a biological sample), or to determine if an amplicon is present following amplification.

Electrophoresis: Electrophoresis refers to the migration of charged solutes or particles in a liquid medium under the influence of an electric field. Electrophoretic separations are widely used for analysis of macromolecules. Of particular importance is the identification of proteins and nucleic acid sequences. Such separations can be based on differences in size and/or charge. Nucleotide sequences have a uniform charge and are therefore separated based on differences in size. Electrophoresis can be performed in an unsupported liquid medium, but more commonly the liquid medium travels through a solid supporting medium. The most widely used supporting media are gels, such as, polyacrylamide and agarose gels (used, for example, in capillary gel electrophoresis and slab gel electrophoresis).

Sieving gels (for example, agarose) impede the flow of molecules. The pore size of the gel determines the size of a molecule that can flow freely through the gel. The amount of time to travel through the gel increases as the size of the molecule increases. As a result, small molecules travel through the gel more quickly than large molecules and thus progress further from the sample application area than larger molecules, in a given time period. Such gels are used for size-based separations of nucleotide sequences.

Fragments of linear DNA migrate through agarose gels with a mobility that is inversely proportional to the $\log_{10}$ of their molecular weight. By using gels with different concentrations of agarose, different sizes of DNA fragments can be resolved. Higher concentrations of agarose facilitate separation of small DNAs, while low agarose concentrations allow resolution of larger DNAs.

Hybridization: Oligonucleotides and their analogs hybridize by hydrogen bonding, which includes Watson-Crick, Hoogsteen or reversed Hoogsteen hydrogen bonding, between complementary bases. "Complementary" refers to the base pairing that occurs between two distinct nucleic acid sequences or two distinct regions of the same nucleic acid sequence.

"Specifically hybridizable," "specifically hybridizes" and "specifically complementary" are terms which indicate a sufficient degree of complementarity such that stable and specific binding occurs between an oligonucleotide and its DNA or RNA target. An oligonucleotide need not be 100% complementary to its target DNA or RNA sequence to be specifically hybridizable. An oligonucleotide is specifically hybridizable when there is a sufficient degree of complementarity to avoid non-specific binding of the oligonucleotide to non-target sequences under conditions in which specific binding is desired, or under conditions in which an assay is performed.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

The following is an exemplary set of hybridization conditions for PCR and is not meant to be limiting:

| Low stringency annealing conditions | |
|---|---|
| Denaturation: | 95° C. for 30 seconds |
| Annealing: | 42° C. for 30 seconds |
| Extension: | 60° C. for 45 seconds |

| High stringency annealing conditions | |
|---|---|
| Denaturation: | 95° C. for 30 seconds |
| Annealing: | 60° C. for 20 seconds |
| Extension: | 72° C. for 15 seconds |

Isolated or purified: An "isolated" or "purified" biological component (such as a nucleic acid, peptide or protein) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its natural environment within a cell. Preferably, a preparation is purified such that the biological component represents at least 50%, such as at least 70%, at least 90%, at least 95%, or greater of the total biological component content of the preparation.

Label: A detectable compound or composition that is conjugated or otherwise attached directly or indirectly to another molecule to facilitate detection of that molecule. Specific, non-limiting examples of labels include radioactive isotopes, enzyme substrates, co-factors, ligands, chemiluminescent or fluorescent markers or dyes, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, 4*th* ed., John Wiley & Sons, Inc., 1999.

Nucleic acid sequence (or polynucleotide): A deoxyribonucleotide or ribonucleotide polymer in either single or double stranded form, and unless otherwise limited, encompasses known analogues of natural nucleotides that hybridize to nucleic acids in a manner similar to naturally occurring nucleotides, and includes polynucleotides encoding full length proteins and/or fragments of such full length proteins which can function as a therapeutic agent. A polynucleotide is generally a linear nucleotide sequence, including sequences of greater than 100 nucleotide bases in length. In one embodiment, a nucleic acid is labeled (for example, biotinylated, fluorescently labeled or radiolabled nucleotides).

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in an oligonucleotide/polynucleotide. A nucleotide sequence refers to the sequence of bases in an oligonucleotide/polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Inosine is also a base that can be integrated into DNA or RNA in a nucleotide (dITP or ITP, respectively).

Oligonucleotide: A nucleic acid molecule generally comprising a length of 300 bases or fewer. The term often refers to single-stranded deoxyribonucleotides, but it can refer as well to single- or double-stranded ribonucleotides, RNA: DNA hybrids and double-stranded DNAs, among others. The term "oligonucleotide" also includes oligonucleosides, that is, an oligonucleotide minus the phosphate. In some examples, oligonucleotides are about 7 to about 50 bases in length, for example, 8, 9, 10, 15, 20, 25, 30, or 35 bases in length. Other oligonucleotides are about 40 or about 45 bases in length.

Oligonucleotides may be single-stranded, for example, for use as probes or primers, or may be double-stranded, for example, for use in the construction of a mutant gene. Oligonucleotides can be either sense or antisense oligonucleotides. An oligonucleotide can be modified as discussed herein in reference to nucleic acid molecules. Oligonucleotides can be obtained from existing nucleic acid sources (for example, genomic or cDNA), but can also be synthetic (for example, produced by laboratory or in vitro oligonucleotide synthesis).

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a peptide, polypeptide, or protein.

Primers and probes: Primers are short nucleic acid molecules, for instance DNA oligonucleotides 7 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs (that is, forward/sense and reverse/antisense) can be used for amplification of a nucleic acid sequence, for example, by the PCR or other nucleic-acid amplification methods known in the art.

A probe includes an isolated nucleic acid sequence attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, 4*th* ed., John Wiley & Sons, Inc., 1999.

Methods for preparing and using nucleic acid primers and probes are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, 4*th* ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50, 75, 90 or more consecutive nucleotides of a target nucleotide sequence.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Sample: A portion, piece, or segment that is representative of the whole from which the sample is obtained. This term encompasses any material, including for instance samples obtained from an animal, a plant, or the environment.

An "environmental sample" includes a sample obtained from inanimate objects or reservoirs within an indoor or outdoor environment. Environmental samples include, but are not limited to: soil, water, dust, and air samples; bulk samples, including building materials, furniture, and landfill contents; and other reservoir samples, such as animal refuse, harvested grains, and foodstuffs. It is to be understood that environmental samples can and often do contain biological components.

A "biological sample" is a sample obtained from a subject, and may also be referred to as a "clinical specimen." As used herein, a biological sample includes all samples useful for detection of enterovirus infection in subjects, including, but not limited to: cells, tissues, and bodily fluids, such as blood; derivatives and fractions of blood (such as serum); extracted galls; biopsied or surgically removed tissue, including tissues that are, for example, unfixed, frozen, fixed in formalin and/or embedded in paraffin; tears; milk; skin scrapes; surface washings; oropharyngeal wash; urine; sputum; cerebrospinal fluid; prostate fluid; semen; pus; bone marrow aspirates; bronchoalveolar lavage (BAL); saliva; nasopharyngeal swabs, eye swabs, cervical swabs, vaginal swabs, and rectal swabs; and stool and stool suspensions.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

III. Overview of Several Embodiments

Provided herein are isolated nucleic acid molecules, which nucleic acid molecules have a nucleotide sequence as set forth in SEQ ID NO: 11, SEQ ID NO: 12, SEQ ID NO: 13, or SEQ ID NO: 14. In certain embodiments, these nucleic acid molecules are EV-specific primers for the detection and identification of EV infection.

Also provided herein in various embodiments is a method of detecting an EV RNA sequence in a sample. In one embodiment, the method includes (i) contacting the sample with one or more nucleic acid cDNA primers that hybridize to an EV VP1 encoding sequence, (ii) reverse transcribing EV cDNA from the EV RNA sequence, (iii) amplifying at least a portion of the EV cDNA using a first nucleic acid primer pair, wherein the first forward primer hybridizes to an EV VP3 encoding sequence and the first reverse primer hybridizes to an EV VP1 encoding sequence, thereby generating an EV amplicon, (iv) amplifying at least a portion of the EV amplicon using a second nucleic acid primer pair, wherein both the second forward and reverse primers hybridize to an EV VP1 encoding sequence, and (v) determining whether an amplified EV amplicon is present, thereby detecting an EV nucleic acid sequence in the sample.

In a specific, non-limiting example of the provided method, the amplification includes a polymerase chain reaction amplification. In another specific, non-limiting example, determining whether an amplified EV amplicon is present includes gel electrophoresis and visualization of the amplified EV amplicon, capillary electrophoresis and detection of the amplified EV amplicon, and/or hybridization of a labeled probe to the amplified EV amplicon. In yet another specific, non-limiting example of the provided method, the one or more nucleic acid cDNA primers include a sequence as set forth in any one of SEQ ID NOs: 1-4, the first forward primer includes a sequence as set forth in SEQ ID NO: 5, the first reverse primer includes a sequence as set forth in SEQ ID NO: 6, the second forward primer includes a sequence as set forth in any one of SEQ ID NOs: 7-11 and 13, and the second reverse primer includes a sequence as set forth in any one of SEQ ID NOs: 6, 12 and 14.

In a further specific example of the provided method, the method includes extracting EV RNA from the sample. In yet a further specific example of the provided method, the method includes electrophoresing and sequencing at least a portion of the amplified EV amplicon, wherein the method of detecting an EV RNA sequence in a sample includes a method of identifying the EV in the sample.

A method of detecting an EV in a biological sample is also described herein. This method includes (i) extracting EV RNA contained in the sample, (ii) contacting the EV RNA with one or more nucleic acid cDNA primers that hybridize to an EV VP1 encoding sequence (iii) reverse transcribing EV cDNA from the EV RNA, (iv) amplifying at least a portion of the EV cDNA using a first nucleic acid primer pair, wherein the first forward primer hybridizes to an EV VP3 encoding sequence and the first reverse primer hybridizes to an EV VP1 encoding sequence, thereby generating an EV amplicon, (v) amplifying at least a portion of the EV amplicon using a second nucleic acid primer pair, wherein both the second forward and reverse primers hybridize to an EV VP1 encoding sequence, and (vi) determining whether an amplified EV amplicon is present, thereby detecting an EV in the biological sample.

In a specific, non-limiting example of the provided method, the amplification includes a polymerase chain reaction amplification. In another specific, non-limiting example, determining whether an amplified EV amplicon is present includes gel electrophoresis and visualization of the amplified EV amplicon, capillary electrophoresis and detection of the amplified EV amplicon, and/or hybridization of a labeled probe to the amplified EV amplicon. In yet another specific, non-limiting example of the provided method, the one or more nucleic acid cDNA primers include a sequence as set forth in any one of SEQ ID NOs: 1-4, the first forward primer includes a sequence as set forth in SEQ ID NO: 5, the first reverse primer includes a sequence as set forth in SEQ ID NO: 6, the second forward primer includes a sequence as set forth in any one of SEQ ID NOs: 7-11 and 13, and the second reverse primer includes a sequence as set forth in any one of SEQ ID NOs: 6, 12 and 14.

In yet a further specific example of the provided method, the method includes electrophoresing and sequencing at least a portion of the amplified EV amplicon, wherein the method of detecting an EV in a biological sample includes a method of identifying the EV in the sample. In another specific, non-limiting example, the biological sample contains free EV particles and/or EV infected cells.

Kits are also disclosed herein that include one or more nucleic acid cDNA primers that hybridize to an EV VP1 encoding sequence, a first PCR nucleic acid primer pair, wherein the first forward PCR primer hybridizes to an EV VP3 encoding sequence and the first reverse PCR primer hybridizes to an EV VP1 sequence, and a second PCR nucleic acid primer pair, wherein both the second forward and reverse PCR primers hybridize to an EV VP1 encoding sequence.

In one embodiment, the one or more nucleic acid cDNA primers include a sequence as set forth in any one of SEQ ID NOs: 1-4. In another embodiment, the first forward PCR primer includes a sequence as set forth in SEQ ID NO: 5 and the first reverse PCR primer includes a sequence as set forth in SEQ ID NO: 6. In still another embodiment, the second forward PCR primer includes a sequence as set forth in any one of SEQ ID NOs: 7-11 and 13 and the second reverse PCR primer includes a sequence as set forth in any one of SEQ ID NOs: 6, 12 and 14. In yet another embodiment, the one or more nucleic acid cDNA primers include a sequence as set forth in any one of SEQ ID NOs: 1-4, the first forward PCR primer includes a sequence as set forth in SEQ ID NO: 5, the first reverse PCR primer includes a sequence as set forth in SEQ ID NO: 6, the second forward PCR primer includes a sequence as set forth in SEQ ID NO: 11, and the second reverse PCR primer includes a sequence as set forth in SEQ ID NO: 12.

IV. Synthesis of Oligonucleotide Primers and Probes

In vitro methods for the synthesis of oligonucleotides are well known to those of ordinary skill in the art; such methods can be used to produce primers and probes for the disclosed methods. The most common method for in vitro oligonucleotide synthesis is the phosphoramidite method, formulated by Letsinger and further developed by Caruthers (Caruthers et al., *Chemical synthesis of deoxyoligonucleotides*, in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach*, IRL Press, 1984.

In general, the synthesis reactions proceed as follows: A dimethoxytrityl or equivalent protecting group at the 5' end of the growing oligonucleotide chain is removed by acid treatment. (The growing chain is anchored by its 3' end to a solid support such as a silicon bead.) The newly liberated 5' end of the oligonucleotide chain is coupled to the 3'-phosphoramidite derivative of the next deoxynucleoside to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500,707, 4,973,679, and 5,132,418. Oligonucleotide synthesizers that employ this or similar methods are available commercially (for example, the PolyPlex oligonucleotide synthesizer from Gene Machines, San Carlos, Calif.). In addition, many companies will perform such synthesis (for example, Sigma-Genosys, The Woodlands, Tex.; Qiagen Operon, Alameda, Calif.; Integrated DNA Technologies, Coralville, Iowa; and TriLink BioTechnologies, San Diego, Calif.).

V. Detection and Identification of Enteroviruses

A major application of the EV-specific primers presented herein is in the area of detection and diagnostic testing for EV infection. Methods for screening a subject to determine if the subject is infected with an EV are disclosed herein.

One such method includes providing a sample, which sample includes an EV or an EV nucleic acid (such as RNA), and providing an assay for detecting in the sample the presence of the EV or EV RNA sequence. Suitable samples include all biological samples useful for detection of viral infection in subjects, including, but not limited to, cells, tissues (for example, lung, liver and kidney), bodily fluids (for example, blood, serum, urine, saliva, sputum, and cerebrospinal fluid), bone marrow aspirates, BAL, oropharyngeal wash, nasopharyngeal swabs, eye swabs, cervical swabs, vaginal swabs, rectal swabs, stool, and stool suspensions. Additional suitable samples include all environmental samples useful for detection of viral presence in the environment, including, but not limited to, a sample obtained from inanimate objects or reservoirs within an indoor or outdoor environment. The detection in the sample of the EV or EV RNA sequence may be performed by a number of methodologies, non-limiting examples of which are outlined below.

In one embodiment, detecting in the sample the presence of an EV or EV RNA sequence includes the extraction of EV RNA. RNA extraction relates to releasing RNA from a latent or inaccessible form in a virion, cell or sample and allowing the RNA to become freely available. In such a state, it is suitable for effective amplification by reverse transcription and the use of, for example, PCR. Releasing RNA may include steps that achieve the disruption of virions containing viral RNA, as well as disruption of cells that may harbor such virions. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral components, wherein such components may be either particulate or dissolved.

One of ordinary skill in the art will know suitable methods for extracting RNA from a sample; such methods will depend upon, for example, the type of sample in which the EV RNA is found. For example, the RNA may be extracted using guanidinium isothiocyanate, such as the single-step isolation by acid guanidinium isothiocyanate-phenol-chloroform extraction of Chomczynski et al. (*Anal. Biochem.* 162:156-59, 1987). Alternatively, an EV virion may be disrupted by a suitable detergent in the presence of proteases and/or inhibitors of ribonuclease activity. Additional exemplary methods for extracting RNA are found, for example, in World Health Organization, *Manual for the virological investigation of polio*, World Health Organization, Geneva, 2001.

Figure 1A:
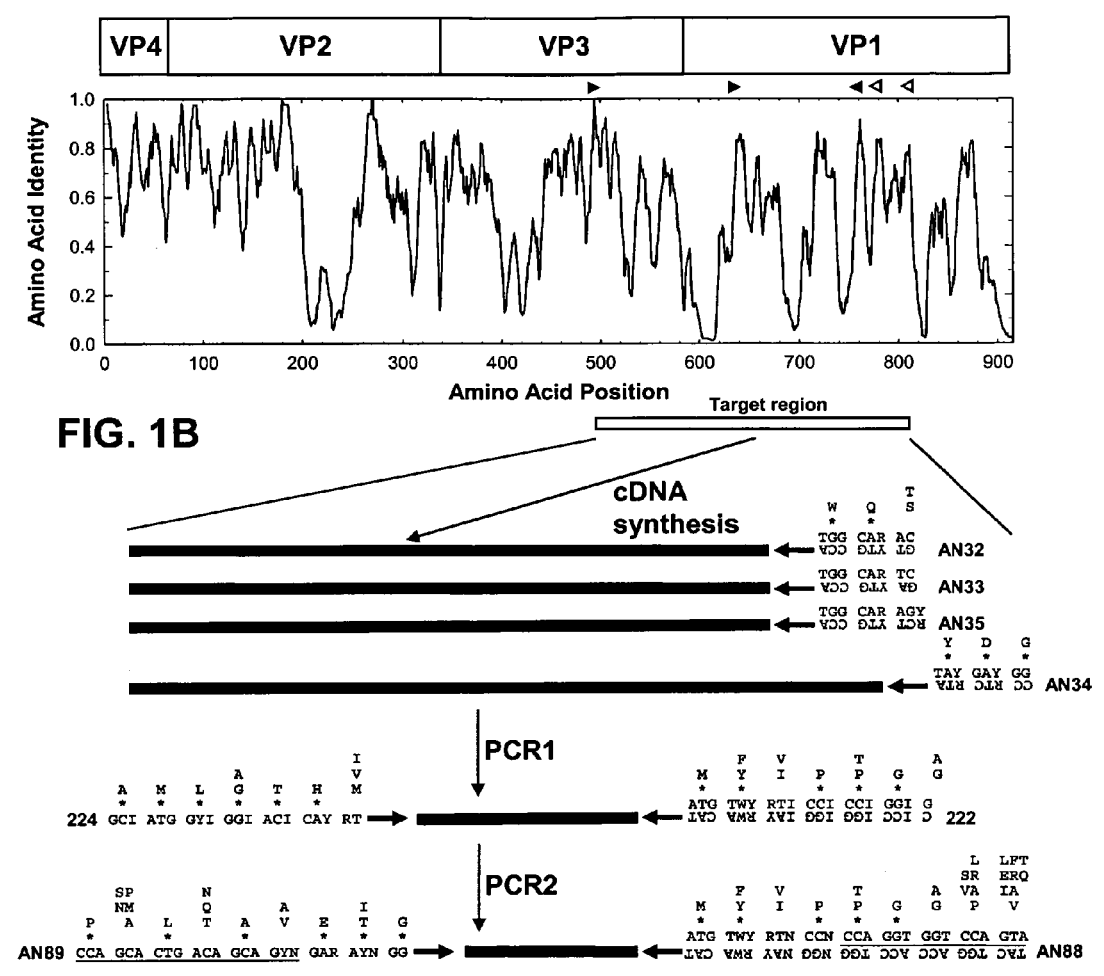

Enterovirus RNA is subjected to reverse transcription to prepare a cognate cDNA that encompasses the region of the genome chosen for detecting and identifying the EV serotype (for example, the region encoding VP1). In one embodiment, a set of random oligonucleotide primers is used, such that certain of the primers in the set will hybridize to the EV RNA and yield one or more cDNA molecules from the virus encompassing the required serotype-specific nucleotide sequence. In another embodiment, gene-specific primers based on conserved amino acid motifs in aligned sequences of known EV serotypes (such as SEQ ID NOs: 1-4) are used for reverse transcription. Subsequently, the EV cDNA is amplified using a suitable amplification protocol to generate an EV amplicon. Any nucleic acid amplification method can be used. In one specific, non-limiting example, PCR is used to amplify the EV cDNA. In another non-limiting example, RT-PCR can be used to amplify the EV cDNA. In an additional non-limiting example, RT-snPCR can be used to amplify the EV cDNA. RT-snPCR refers to a pair of PCRs (PCR1 and PCR2) that is initiated with cDNA that has been reverse transcribed from RNA, and is run in series, each with a pair of primers flanking the same sequence. The first PCR(PCR1) amplifies a sequence, such as an EV cDNA sequence. The second primer pair (semi-nested primers) for the second PCR (PCR2) bind at one end of and within the first PCR product and produce a second PCR product that is shorter than the first one (see FIG. 1B). Techniques for reverse transcription and nucleic acid amplification are well-known to those of skill in the art.

In some embodiments, pairs of EV-specific primers are utilized in the RT-snPCR amplification reaction. Specific, non-limiting examples of EV-specific primers include, but are not limited to: 224 (SEQ ID NO: 5), 222 (SEQ ID NO: 6), 187 (SEQ ID NO: 7), 188 (SEQ ID NO: 8), 189 (SEQ ID NO: 9), 292 (SEQ ID NO: 10), AN89 (SEQ ID NO: 11), AN88 (SEQ ID NO: 12), AN79 (SEQ ID NO: 13), and AN78 (SEQ ID NO: 14).

Enterovirus amplicons obtained following nucleic acid amplification can be sequenced to determine the nucleotide sequence in each. Procedures that can be used for sequencing include the methods of Maxam and Gilbert (*Meth. Enzymol.* 65:499-566, 1980) and Sanger et al. (*Proc. Natl. Acad. Sci. USA* 74:5463-67, 1977). Sequencing methods are also discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The method of Sanger et al. involves the use of different 2',3'dideoxynucleotide chain terminators in each of four template-driven DNA polymerase reactions, and is readily implemented in automated sequencing instruments, such as those of MJ Research, Inc. (San Francisco, Calif.), Stratagene (La Jolla, Calif.), or Applied Biosystems (Foster City, Calif.).

Enterovirus amplicon sequences can be compared with the sequences of EV reference strains (such as VP1 sequence of EV reference strains), including at least one representative of each recognized serotype, in order to identify (serotype) the EV. One of ordinary skill in the art will know suitable methods for comparing sequences. For example, script-driven sequential pairwise comparison using the program Gap, (Wisconsin Sequence Analysis Package, version 10.2, Accelrys, Inc., San Diego, Calif.) can be used to compare EV amplicon sequences to EV reference strains.

The subject matter of the present disclosure is further illustrated by the following non-limiting Examples.

EXAMPLES

Example 1

Primer Design and Construction

This example describes the design and construction of primers for amplification and identification of EVs, particularly EVs in clinical specimens.

Consensus degenerate primers for the cDNA and PCR1 steps were designed from conserved amino acid motifs in the aligned capsid sequences of the 64 EV serotype prototype strains (Table 1; FIG. 1). The four cDNA primers (AN32, AN33, AN34, and AN35) were designed to anneal to conserved sites downstream of the reverse PCR primer; these sites encode the motifs, WQT (AN32, SEQ ID NO: 1), WQS (AN33, SEQ ID NO: 2 and AN35, SEQ ID NO: 4), and YDG (AN34, SEQ ID NO: 3) (Table 2; FIG. 1). PCR1 forward primer 224 (SEQ ID NO: 5) was designed to target the site in VP3 encoding the highly conserved motif AMLGTH(I/L/M) (SEQ ID NO: 19) (Table 2; FIG. 1), while PCR1 reverse primer 222 (SEQ ID NO: 6) targets a conserved motif M(F/Y)(I/V)PPG(A/G) (SEQ ID NO: 20), near the middle of VP1 (Table 2; FIG. 1; Oberste et al., *J. Clin. Microbiol.* 38:1170-74, 2000). These two motifs are conserved among all EV serotypes. The degenerate primer design approach was used for the PCR1 primers to broaden the specificity of amplification, allowing amplification of all EV serotypes and increasing the absolute concentration of virus-specific product to be used as template for PCR2. The presence of inosine residues in positions of four-fold codon degeneracy reduces the overall degeneracy of the PCR1 primers but also results in decreased thermostability of the primer-template helix. As a result, low stringency annealing conditions are required for PCR1.

One pair of internal primers used in PCR2 included forward internal primer 292 (SEQ ID NO: 10), which targets the conserved motif (Q/T)A(A/V)ETG (SEQ ID NO: 21), paired with reverse primer 222 (SEQ ID NO: 6) (Table 2; FIG. 1). Additional internal primers used in PCR2 were designed without the use of inosine residues, using the CODEHOP strategy (Rose et al., *Nucl. Acids. Res.* 26:1628-35, 1998), and with target sites encoding conserved motifs in VP1. These included forward PCR2 primer AN89 (SEQ ID NO: 11), which targets the conserved motif PALTA(A/V)E(I/T)G (SEQ ID NO: 22), paired with reverse PCR2 primer AN88 (SEQ ID NO: 12), which targets the conserved motif M(F/Y)(I/V)PPGGPV (SEQ ID NO: 23) (Table 2; FIG. 1). The consensus clamp and increased length both contribute to the increased thermostability of primers AN88 (SEQ ID NO: 12) and AN89 (SEQ ID NO: 11), compared with, for example, primers 292 (SEQ ID NO: 10) and 222 (SEQ ID NO: 6).

TABLE 1

Reference strains of 64 recognized EV serotypes, 15 additional variant reference strains (italicized) and 22 proposed new serotypes (EV73 Henderson - EV101).

| Strain | dbGAP % nuc. identity | Source and Date | Comments |
| --- | --- | --- | --- |
| CA1 Tompkins | 100 | SM 9+ Apr. 6, 1981 | |
| CA2 Fleetwood | 99 | SM 10+ May 6, 1981 | |
| CA3 Olsen | 100 | SM 8+ Apr. 6, 1981 | |
| CA4 High Point | 79 | SM 1+ Apr. 6, 1981 | |
| CA5 Swartz | 100 | SM 9+ May 6, 1981 | |
| CA6 Gadula | 100 | SM 4+ Apr. 6, 1981 | |
| CA7 AB-IV | 99 | RD2 Feb. 14, 1984 | |
| CA8 Donovan | 100 | SM 10+ May 6, 1981 | |
| CA9 Griggs | 98 | MK 2+ Mar. 16, 1982 | |
| CA10 Kowalik | 100 | SM 8+ Apr. 13, 1981 | |
| CA11 Belgium-1 | 100 | SM 9+ May 6, 1981 | |
| CA12 Texas-12 | 100 | SM 7+ May 13, 1981 | |
| CA13 Flores | 99 | SM 9+ Apr. 14, 1981 | |
| CA14 G-14 | 84 | RD Aug. 28, 2002 | |

TABLE 1-continued

Reference strains of 64 recognized EV serotypes, 15 additional variant reference strains (italicized) and 22 proposed new serotypes (EV73 Henderson - EV101).

| Strain | dbGAP % nuc. identity | Source and Date | Comments |
|---|---|---|---|
| CA15 G-9 | 100 | SM 1 Jul. 6, 1981 | |
| CA16 G-10 | 95 | Mar. 30, 1981 | |
| CA17 G-12 | 100 | SM 9+ Jun. 8, 1981 | |
| CA18 G-13 | 100 | SM 7+ Jul. 16, 1974 | |
| CA19 8663 | 100 | SM 9+ Apr. 14, 1981 | |
| CA20 IH-35 | 99 | SM 10+ Aug. 17, 1981 | |
| CA21 Kuykendall | 95 | RD3 Aug. 14, 2002 | |
| CA22 Chulman | 100 | SM 8+ Jul. 6, 1981 | |
| CA24 Joseph | 100 | SM 10+ Mar. 5, 1990 | |
| *CA24v EH24* | 78 | RD Sep. 21, 1983 | *Comparison to CA24 Joseph* |
| CB1 Conn-5 | 78 | MK 14+-LLCMK2 1 Apr. 30, 1999 | |
| CB2 Ohio-1 | 99 | MK 12+-BGM 1 Jul. 2, 1984 | |
| CB3 Nancy | 98 | HELF 2-MK Aug. 12, 1980 | |
| CB4 JVB | 81 | MK 4+-LLGMK2 1 Jun. 19, 1991 | |
| CB5 Faulkner | 75 | LLCMK2 2 Jan. 18, 1998 | |
| CB6 Schmitt | 100 | MK 10+ May 2, 1979 | |
| E1 Farouk | 99 | MK 2+ May 6, 1981 | |
| E2 Cornelis | 100 | MK 14+ May 2, 1979 | |
| E3 Morrisey | 100 | MK 14+ May 6, 1981 | |
| *E4 Du Toit* | 82 | MK 6+ Feb. 16, 1982 | *Comparison to Pesacek* |
| *E4 Shropshire* | 82 | MK 6+ Jan. 9, 1980 | *Comparison to Pesacek* |
| E4 Pesacek | 100 | | |
| E5 Noyce | 99 | MK 14+ Feb. 16, 1982 | |
| *E6 D'Amori* | 100 | MK 14+ Apr. 30, 1985 | |
| *E6' Cox* | 77 | MK 6+ Feb. 16, 1982 | |
| *E6" Burgess* | 98 | MK 5+ Mar. 1, 1982 | |
| E6 Charles | 100 | | |
| E7 Wallace | 98 | MK 19+ Aug. 19, 1986 | |
| *E8 Bryson* | 76 | MK 19+ Mar. 1, 1982 | *Comparison to E1* |
| E9 Hill | 97 | MK 20+-LLCMK2 1 Jun. 14, 1991 | |
| E11 Gregory | 100 | MK 11+ Oct. 22, 1984 | |
| *E11' Silva* | 75 | MK 7+ May 6, 1981 | *Comparison to Gregory* |
| E12 Travis | 100 | MK 14+ Feb. 6, 1984 | |
| E13 Del Carmen | 99 | MK 15+ Mar. 1, 1982 | |
| E14 Tow | 100 | MK 15+ Mar. 1, 1982 | |
| E15 CH96-51 | 100 | MK13+ May 6, 1981 | |
| E16 Harrington | 99 | MK19+ Apr. 25, 1984 | |
| E17 CHHE-29 | 100 | MK 17+ Jul. 30, 1981 | |
| E18 Metcalf | 99 | MK 18+ Mar. 16, 1982 | |
| E19 Burke | 100 | MK 20+ May 12, 1981 | |
| E20 JV-1 | 100 | MK 1+ May 5, 1976 | |
| E21 Farina | 100 | MK 18+ HELF 2 Aug. 18, 1975 | |
| E24 De Comp | 100 | MK 9-BGM 3/76 | |
| E25 JV-4 | 100 | MK 13+ Jun. 24, 1981 | |
| E26 Coronel | 100 | MK 13+ Jun. 24, 1981 | |
| E27 Bacon | 100 | MK 13+ Jul. 25, 1988 | |
| E29 JV-10 | 100 | | |
| E30 Bastianni | 99 | MK 13+ Aug. 27, 1984 | |
| *E30 Frater* | 88 | HELF 1 Jul. 30, 1981 | *Comparison to Gregory* |
| *E30 Giles* | 77 | HELF 1 Oct. 14, 1982 | *Comparison to Gregory* |
| *E30 PR-17* | 76 | | *Comparison to Gregory* |
| E31 Caldwell | 100 | MK 6+ Mar. 16, 1982 | |
| E32 PR-10 | 100 | MK 6+ May 12, 1981 | |
| E33 Toluca-3 | 100 | MK 6+ May 12, 1981 | |
| *E34 DN-19* | 80 | HELF 1 Sep. 7, 1984 | *Comparison to CA24 Joseph* |
| EV68 Fermon | 98 | HELF 2 Jul. 7, 1978 | |
| EV69 Toluca-1 | 100 | HELF 5 Feb. 22, 1982 | |
| EV70 J670/71 | 100 | HELF 4 Sep. 7, 1984 | |
| EV71 BrCr | 100 | HELF 2 May 21, 1999 | |
| PV1 Mahoney | 100 | | |
| *PV1 Sabin* | 98 | | *Comparison to Mahoney* |
| PV2 Lansing | 84 | | |
| *PV2 Sabin* | 81 | | |

TABLE 1-continued

Reference strains of 64 recognized EV serotypes, 15 additional variant reference strains (italicized) and 22 proposed new serotypes (EV73 Henderson - EV101).

| Strain | dbGAP % nuc. identity | Source and Date | Comments |
|---|---|---|---|
| PV3 Leon | 100 | | |
| *PV3 Sabin* | 98 | | *Comparison to PV3 Leon* |
| EV73 Henderson | 100 | | |
| EV74 | 100 | | |
| EV75 | 100 | | |
| EV76 | 99 | | |
| EV79 | 100 | | |
| EV80 | 100 | | |
| EV81 | 100 | | |
| EV82 | 100 | | |
| EV83 | 100 | | |
| EV84 | 100 | | |
| EV85 | 100 | | |
| EV86 | 100 | | |
| EV87 | 100 | | |
| EV88 | 100 | | |
| EV89 | 100 | | |
| EV90 | 100 | | |
| EV91 | 99 | | |
| EV92 | 100 | | |
| EV96 | 89 | | |
| EV97 | 99 | | |
| EV100 | 100 | | |
| EV101 | 99 | | |

TABLE 2

Primers

| Primer | Sequence | Amino acid motif | Gene | Location[a] |
|---|---|---|---|---|
| AN32 | GTYTGCCA (SEQ ID NO: 1) | WQT | VP1 | 3009-3002 |
| AN33 | GAYTGCCA (SEQ ID NO: 2) | WQS | VP1 | 3009-3002 |
| AN34 | CCRTCRTA (SEQ ID NO: 3) | YDG | VP1 | 3111-3104 |
| AN35 | RCTYTGCCA (SEQ ID NO: 4) | WQS | VP1 | 3009-3002 |
| 224 | GCIATGYTIGGIACICAYRT (SEQ ID NO: 5) | AMLGTH(I/L/M) (SEQ ID NO: 19) | VP3 | 1977-1996 |
| 222 | CICCIGGIGGIAYRWACAT (SEQ ID NO: 6) | M(F/Y)(I/V)PPG(A/G) (SEQ ID NO: 20) | VP1 | 2969-2951 |
| 187 | ACIGCIGYIGARACIGGNCA (SEQ ID NO: 7) | TA(A/V)ETGH (SEQ ID NO: 21) | VP1 | 2612-2631 |
| 188 | ACIGCIGTIGARACIGGNG (SEQ ID NO: 8) | TAVETG(A/V) (SEQ ID NO: 22) | VP1 | 2612-2630 |
| 189 | CARGCIGCIGARACIGGNGC (SEQ ID NO: 9) | QAAETGA (SEQ ID NO: 23) | VP1 | 2612-2631 |
| 292 | MIGCIGYIGARACNGG (SEQ ID NO: 10) | (Q/T)A(A/V)ETG (SEQ ID NO: 24) | VP1 | 2612-2627 |
| AN89 | *CCAGCACTGACAGCAGYNGARAYNGG*[b] (SEQ ID NO: 11) | PALTA(A/V)E(I/T)G (SEQ ID NO: 25) | VP1 | 2602-2627 |
| AN88 | *TACTGGACCACCTGGNGGNAYRWACAT*[b] (SEQ ID NO: 12) | M(F/Y)(I/V)PPGGPV (SEQ ID NO: 26) | VP1 | 2977-2951 |
| AN79 | *GAAGTACCAGCACTGACAGCAGYI GARAYNGG* (SEQ ID NO: 13) | EVPALTA(A/V)E(I/T)G (SEQ ID NO: 27) | VP1 | 2596-2627 |

TABLE 2-continued

Primers

| Primer | Sequence | Amino acid motif | Gene | Location[a] |
|---|---|---|---|---|
| AN78 | CTGTTTGGTACTGGACCACCTGG IGGIAYRWACAT (SEQ ID NO: 14) | VWM(F/Y)(I/V)PPGGPV (SEQ ID NO: 28) | VP1 | 2969-2951 |
| AN232 | CCAGCACTGACAGCA[b] (SEQ ID NO: 15) | PALTA (SEQ ID NO: 29) | VP1 | 2602-2616 |
| AN233 | TACTGGACCACCTGG[b] (SEQ ID NO: 16) | PGGPV (SEQ ID NO: 30) | VP1 | 2977-2963 |
| AN230 | *AATTAACCCTCACTAAAGGGAGAAGATA* TTATACTCAYTGG[c] (SEQ ID NO: 17) | RYYTHW (SEQ ID NO: 31) | VP3 | 1993-2010 |
| AN231 | GTCAGCTGGGTTTATNCCRTA (SEQ ID NO: 18) | YGINPAD (SEQ ID NO: 32) | VP1 | 3069-3049 |

[a]Location relative to the genome of PV1-Mahoney (GenBank accession number J02281), except for AN230 and AN231, whose locations are relative to the genome of EV68-Fermon (GenBank accession number AY426531).
[b]AN232 is the non-degenerate "clamp" portion of AN89 and AN233 is the non-degenerate clamp portion of AN88. Within the AN88 and AN89 sequences, these clamp regions are indicated by italic type.
[c]The T3 RNA polymerase promoter sequence is underlined. IUB ambiguity codes: R = A or G; Y = C or T; W = A or T; N = A, C, G, or T; M = A or C; I = Inosine.

Example 2

Detection and Identification of Enteroviruses

This example describes how enterovirus-specific nucleic acids can be amplified and detected using specific primers.

Nucleic acid from all 64 EV serotype reference strains, 15 additional reference strains for some serotypes and 22 proposed new serotypes (Table 1; 101 strains total) was extracted with the QIAamp Viral RNA Mini Kit (Qiagen, Inc., Valencia, Calif.), which was used according to the manufacturer's instructions. Eluted RNAs were dried passively in a bench top desiccator under vacuum. The dried RNA was resuspended in 16 µl of sterile nuclease-free water and stored at −20° C. until use.

Synthesis of cDNA was carried out in a 10 µl reaction containing 5 µl of RNA, 100 mM each dNTP (Amersham Biosciences, Piscataway, N.J.), 2 µl of 5× reaction buffer (Invitrogen, Carlsbad, Calif.), 0.01 M dithiothreitol (DTT), 1 pmol each cDNA primer (AN32 (SEQ ID NO: 1), AN33 (SEQ ID NO: 2), AN34 (SEQ ID NO: 3), and AN35 (SEQ ID NO: 4); Table 2), 20 U of RNasin (Promega Corp., Madison, Wis.), and 100 U of Superscript II reverse transcriptase (Invitrogen, Carlsbad, Calif.). Following incubation at 22° C. for 10 min, 45° C. for 45 min, and 95° C. for 5 min, the entire 10 µl RT reaction was then used in the first PCR reaction (50 µl final volume) (PCR1), consisting of 5 µl of 10×PCR buffer (Roche Applied Science, Indianapolis, Ind.), 200 µM each dNTP, 50 pmol each of primers 224 (SEQ ID NO: 5) and 222 (SEQ ID NO: 6) (Table 2), and 2.5 U of Taq DNA polymerase (Roche Applied Science, Indianapolis, Ind.), with 40 cycles of amplification (95° C. for 30 s, 42° C. for 30 s, 60° C. for 45 s). One microliter of the first PCR reaction was added to a second PCR reaction (PCR2) for semi-nested amplification. PCR2 contained 40 pmol each of primers AN89 (SEQ ID NO: 11) and AN88 (SEQ ID NO: 12) (Table 2), 200 µM each dNTP, 5 µl of 10× FastStart Taq buffer (Roche Applied Science, Indianapolis, Ind.), and 2.5 U of FastStart Taq DNA polymerase (Roche Applied Science, Indianapolis, Ind.) in a final volume of 50 µl. The FastStart Taq polymerase was activated by incubation at 95° C. for 6 min prior to 40 amplification cycles of 95° C. for 30 s, 60° C. for 20 s, and 72° C. for 15 s. Reaction products were separated and visualized on 1.2% agarose gels, containing 0.5 µg ethidium bromide per ml, and purified from the gel by using the QIAquick Gel Extraction Kit (Qiagen, Inc., Valencia, Calif.). The resulting DNA templates were sequenced with the Big Dye Terminator v1.1 Ready Reaction Cycle Sequencing Kit on an ABI Prism 3100 automated sequencer (both from Applied Biosystems, Foster City, Calif.), using primers AN89 (SEQ ID NO: 11) and AN88 (SEQ ID NO: 12) or primers AN232 (SEQ ID NO: 15) and AN233 (SEQ ID NO: 16) (Table 2).

Amplicon sequences were compared with the VP1 sequences of EV reference strains, including at least one representative of each recognized serotype, by script-driven sequential pairwise comparison using the program Gap (Wisconsin Sequence Analysis Package, version 10.2, Accelrys, Inc., San Diego, Calif.), as described by Oberste et al. (*J. Gen. Virol.* 86:445-51, 2005; *J. Gen. Virol.* 85:3205-12, 2004; *J. Clin. Virol.* 26:375-77, 2003). In cases where the result was not unequivocal (highest score less than 75% or second-highest score greater than 70%), deduced amino acid sequences were compared using a similar method.

All 64 EV serotype reference strains, 15 additional reference strains for some serotypes and 22 proposed new serotypes (Table 1; 101 strains total) were successfully amplified and sequenced using the CODEHOP VP1 RT-snPCR procedure (FIG. 2). Slight variations in the sizes of the PCR products were observed due to VP1 gene length differences in the different serotypes, as described by Oberste et al. (*J. Virol.* 73:1941-48, 1999; *J. Clin. Virol.* 26:375-77, 2003). All 87 clinical isolates (Table 3) tested were also successfully amplified, sequenced, and identified by comparing the nucleic acid sequence to an EV reference strain VP1 sequence database (see Example 4 herein). In all cases, the serotype based on the VP1 RT-snPCR amplicon was identical to the serotype previously determined by neutralization or by VP1 sequencing using different primers and conventional PCR (Oberste et al., *J. Clin. Microbiol.* 38:1170-74, 2000; Oberste et al., *J. Clin. Microbiol.* 37:1288-93, 1999).

TABLE 3

Clinical Isolates

| EV Code | Country | Year | Serotype | VP1 RT-snPCR | % Nucleotide ID | % Protein ID |
|---|---|---|---|---|---|---|
| 10052 | USA-TX | 1992 | CA14 | CA14 | 82.7 | NA |
| 10053 | USA-AZ | 1994 | CA14 | CA14 | 83.5 | NA |
| 10055 | TAI | 1984 | CA16 | CA16 | 77.3 | NA |
| 10056 | USA-PA | 1989 | CA16 | CA16 | 78.1 | NA |
| 10057 | USA-GA | 1995 | CA16 | CA16 | 78.8 | NA |
| 10058 | USA-TX | 1995 | CA16 | CA16 | 77.7 | NA |
| 10061 | MOR | 1983 | CA20 | CA20 | 81.5 | NA |
| 10062 | MOR | 1983 | CA20 | CA20 | 81.5 | NA |
| 10063 | USA-MD | 1986 | CA21 | CA21 | 93.1 | NA |
| 10064 | GUT | 1988 | CA21 | CA21 | 76 | NA |
| 10066 | USA-WA | 1989 | CA21 | CA21 | 91.5 | NA |
| 10067 | USA-AZ | 1994 | CA21 | CA21 | 90.6 | NA |
| 10068 | USA-GA | 1995 | CA21 | CA21 | 92.5 | NA |
| 10069 | USA-TX | 1996 | CA21 | CA21 | 91.6 | NA |
| 10070 | USA-GA | 1984 | CA24 | CA24 | 73.7 | NA |
| 10072 | USA-GA | 1993 | CA9 | CA9 | 85.8 | NA |
| 10073 | USA-GA | 1996 | CA9 | CA9 | 84.9 | NA |
| 10074 | USA-MD | 1984 | CB2 | CB2 | 83 | NA |
| 10077 | USA-FL | 1992 | CB2 | CB2 | 81.3 | NA |
| 10078 | USA-NC | 1995 | CB2 | CB2 | 83.8 | NA |
| 10080 | BRA | 1988 | CB3 | CB3 | 78.6 | NA |
| 10082 | BRA | 1988 | CB3 | CB3 | 78.8 | NA |
| 10083 | BRA | 1988 | CB3 | CB3 | 78.6 | NA |
| 10084 | PER | 1989 | CB3 | CB3 | 76.6 | NA |
| 10085 | USA-NM | 1993 | CB3 | CB3 | 75.8 | NA |
| 10086 | USA-NH | 1997 | CB3 | CB3 | 75.3 | NA |
| 10088 | HON | 1988 | CB4 | CB4 | 81 | NA |
| 10090 | USA-MD | 1986 | CB5 | CB5 | 97.2 | NA |
| 10091 | USA-PA | 1988 | CB5 | CB5 | 84 | NA |
| 10092 | MEX | 1988 | CB5 | CB5 | 83.6 | NA |
| 10093 | USA-ME | 1993 | CB5 | CB5 | 93.4 | NA |
| 10096 | USA-WA | 1992 | E11 | E11 | E11 76; E19 72.3; E5 70.4 | E11 89; E19 77.6; E5 70.1 |
| 10097 | USA-GA | 1992 | E11 | E11 | E11 77.6; E19 72; CA9 70 | E11 89.7; E19 78.5; CA9 75.7 |
| 10098 | USA-FL | 1993 | E11 | E11 | E11 76.9; E19 71.3; E7 70.1 | E11 89.7; E19 78.5; E7 75.7 |
| 10099 | USA-VA | 1995 | E11 | E11 | E11 77.6; E19 71.7; E7 70.1 | E11 88.8; E19 77.6; E7 75.7 |
| 10100 | PER | 1998 | E11 | E11 | E11 81.3; E19 72.9 | E11 95.3; E19 80.4 |
| 10101 | ELS | 1988 | E12 | E12 | E12 79.4; E3 73.3; E14 71.7 | E12 99; E3 86.4; E14 70.9 |
| 10102 | USA-VA | 1986 | E13 | E13 | E13 73.5; EV69 71 | E3 87.9; EV69 83.2 |
| 10103 | USA-TX | 1995 | E13 | E13 | E13 72.6; EV69 73.2 | E13 87.9; EV69 83.2 |
| 10105 | USA-OR | 1985 | E18 | E18 | 81.6 | NA |
| 10106 | USA-SC | 1987 | E18 | E18 | 80.7 | NA |
| 10107 | USA-MD | 1988 | E18 | E18 | 80.4 | NA |
| 10108 | USA-OK | 1989 | E18 | E18 | 80.7 | NA |
| 10109 | USA-CT | 1996 | E18 | E18 | 81.2 | NA |
| 10110 | USA-TX | 1997 | E18 | E18 | 81.6 | NA |
| 10111 | USA-RI | 1994 | E21 | E21 | E21 80.6; E30 71.9 | E21 97.2; E30 81.5 |
| 10112 | USA-NC | 1983 | E24 | E24 | 78.9 | NA |
| 10114 | USA-NC | 1984 | E25 | E25 | 79.7 | NA |
| 10115 | HON | 1986 | E25 | E25 | 79.1 | NA |
| 10116 | USA-MD | 1992 | E25 | E25 | E25 80.1; EV73 70.8 | E25 91.6; EV73 73.1 |
| 10117 | USA-MO | 1993 | E25 | E25 | 79.9 | NA |
| 10118 | USA-OR | 1993 | E25 | E25 | E25 79.8; EV73 70.4 | E25 93.6; EV73 73.6 |
| 10119 | USA-MN | 1994 | E25 | E25 | E25 81; EV73 70.2 | E25 94.4; EV73 74 |
| 10120 | PER | 1988 | E29 | E29 | 78.4 | NA |
| 10122 | USA-MT | 1987 | E3 | E3 | E3 83.8; E12 73.2 | E3 98.1; E12 85 |
| 10123 | USA-MD | 1988 | E3 | E3 | E3 84.7; E12 74.5; E14 70.4 | E3 99.1; E12 85.9; E14 74.8 |
| 10124 | USA-WA | 1994 | E3 | E3 | E3 82.1; E12 73 | E3 94.7; E12 82.1 |

TABLE 3-continued

Clinical Isolates

| EV Code | Country | Year | Serotype | VP1 RT-snPCR | % Nucleotide ID | % Protein ID |
|---|---|---|---|---|---|---|
| 10125 | USA-OR | 1991 | E30 | E30 | E30 81.5; E21 71.6 | E30 89.8; E21 77.8 |
| 10126 | USA-AR | 1994 | E30 | E30 | E30 82.4; E21 71 | E30 90.7; E21 78.7 |
| 10127 | USA-GA | 1993 | E30 | E30 | E30 81.8; E21 71.6 | E30 90.7; E21 78.7 |
| 10128 | USA-VA | 1995 | E30 | E30 | E30 82.4; E21 71 | E30 90.7; E21 78.7 |
| 10129 | PER | 1998 | E33 | E33 | 76.9 | NA |
| 10131 | USA-PA | 1988 | E4 | E4 | 81.6 | NA |
| 10132 | USA-WA | 1993 | E4 | E4 | 82.6 | NA |
| 10133 | USA-CT | 1996 | E5 | E5 | 84.9 | NA |
| 10134 | USA-WA | 1991 | E6 | E6 | 78.1 | NA |
| 10135 | USA-NM | 1995 | E6 | E6 | 77.6 | NA |
| 10136 | PER | 1998 | E6 | E6 | 81 | NA |
| 10137 | USA-GA | 1993 | E7 | E7 | E7 78.2; E19 70.7 | E7 95.3; E19 75.7 |
| 10138 | USA-GA | 1993 | E7 | E7 | E7 78.2; E19 70.7 | E7 95.3; E19 75.7 |
| 10139 | PER | 1998 | E7 | E7 | 78.2 | NA |
| 10140 | USA-NC | 1992 | E9 | E9 | 79 | NA |
| 10141 | USA-AR | 1995 | E9 | E9 | E9 80.4; E5 71.4; E14 71.4 | E9 94.3; E5 71.4; E14 73.3 |
| 10142 | USA-WI | 1995 | E9 | E9 | E9 78; E14 72; E5 71.1 | E9 96.2; E14 74.5; E5 73.6 |
| 10144 | USA-TX | 1989 | EV71 | EV71 | 84.7 | NA |
| 10146 | USA-MD | 1987 | EV71 | EV71 | 81 | NA |
| 10147 | USA-OK | 1989 | EV71 | EV71 | 84.9 | NA |
| 10148 | USA-NM | 1990 | EV71 | EV71 | 83.3 | NA |
| 10149 | USA-NM | 1994 | EV71 | EV71 | 84.4 | NA |
| 10150 | USA-CT | 1994 | EV71 | EV71 | 85 | NA |
| 10151 | USA-MD | 1995 | EV71 | EV71 | 83 | NA |
| 10152 | USA-CA | 1990 | HRV2 | HRV2 | 92.2 | NA |
| 10153 | USA-OK | 1985 | UNT EV | EV75 | 99.7 | NA |
| 10154 | USA-VA | 1986 | UNT EV | EV75 | EV75 86.6; E33 70.1 | EV75 100; E33 72.9 |
| 10155 | USA-CT | 1987 | UNT EV | EV75 | 84 | NA |
| 10156 | USA-CT | 1987 | UNT EV | EV75 | 83.2 | NA |
| 10157 | USA-OK | 1988 | UNT HRV | HRV31 | 89.2 | NA |

NA: not applicable;
UNT: untypable.

Example 3

Assay Sensitivity

This example describes the sensitivity of EV detection/identification methods using specific primers to amplify enterovirus-specific nucleic acids.

Figure 3A:
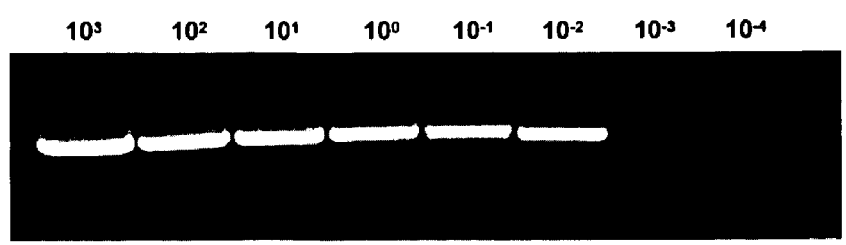
FIGS. 3A-3C illustrate the sensitivity of VP1 RT-snPCR and a show a comparison of VP1 RT-snPCR with 5'-NTR RT-snPCR.

Sensitivity was tested by two methods. Sensitivity relative to cell culture infectivity was measured using a titered stock of the EV68 prototype strain, Fermon. Serial 10-fold dilutions of the EV68-Fermon stock were made in Hank's balanced salt solution, and RNA from 100 µl of each dilution was extracted with the QIAamp Viral RNA Mini Kit (Qiagen, Inc., Valencia, Calif.). RNAs representing from $10^4$ cell culture infectious dose 50% endpoint units ($CCID_{50}$) to $10^{-3}$ $CCID_{50}$ per 5 µl were tested with the VP1 RT-snPCR assay. The VP1 RT-snPCR assay detected RNA extracted from as little as 0.01 $CCID_{50}$ per 5 µl of EV68-Fermon (FIG. 3A), indicating that the assay is at least 100-fold more sensitive than cell culture (since 1 $CCID_{50}$ defines the cell culture endpoint).

Figure 3B:
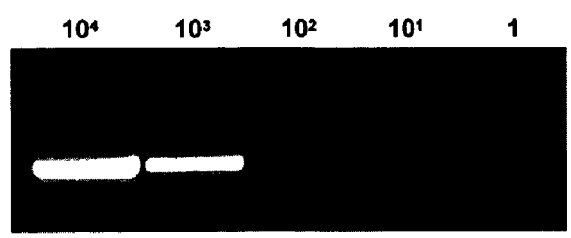

Absolute sensitivity was measured by using an in vitro-transcribed synthetic RNA standard derived from EV68-Fermon. To make the synthetic RNA standard, RT-PCR primers were designed to flank the VP3-VP1 RT-snPCR assay cDNA product. The sense primer AN230 (SEQ ID NO: 17) contains the 23-base T3 RNA polymerase promoter at the 5' end, and it was used with the antisense primer AN231 (SEQ ID NO: 18) (Table 2) in a two-step RT-PCR. cDNA was made with SuperScript II RT (Invitrogen, Carlsbad, Calif.) according to the kit instructions, using 10 pmol AN231 (SEQ ID NO: 18) to prime the cDNA. PCR was performed with FastStart Taq (Roche Applied Science, Indianapolis, Ind.), using the manufacturer's 10× buffer with $MgCl_2$, 2 µl of cDNA, 200 µM each dNTP, and 20 pmol each of AN230 (SEQ ID NO: 17) and AN231 (SEQ ID NO: 18) primers, in a final reaction volume of 50 µl. The thermocycler program consisted of 40 cycles of 95° C. for 30 s, 55° C. for 40 s, and 72° C. for 40 s. The PCR product was purified using the High Pure PCR Product Purification Kit (Roche Applied Science, Indianapolis, Ind.) according to the manufacturer's instructions. Purified PCR product was quantitated spectrophotometrically, and 1 µg of PCR product was used as template for in vitro RNA transcription, using the MEGAscript High Yield Transcription Kit (Ambion, Inc., Austin, Tex.) according to the manufacturer's protocol. The VP3-VP1 single-stranded, positive-sense standard RNA product (VP3-VP1 sRNA; 1082 nt) was digested with DNase I to remove template DNA and then purified with the QIAamp Viral RNA Mini Kit (Qiagen, Inc., Valencia, Calif.). The manufacturer's instructions were followed, except no carrier tRNA was added to the kit's lysis buffer. The purified VP3-VP1 sRNA was quantitated spectrophotometrically, and the concentration was calculated in units of RNA molecules per microliter. Two separate lots of the VP3-VP1 sRNA were synthesized and diluted to contain from $10^4$ copies to 1 copy per 5 µl and then tested in two separate experiments with the VP1 RT-snPCR assay. As few as 10 copies of the in vitro-transcribed VP3-VP1 sRNA produced a detectable gel band in two independent experiments, indicating a low limit of absolute sensitivity (FIG. 3B).

Figure 3C:
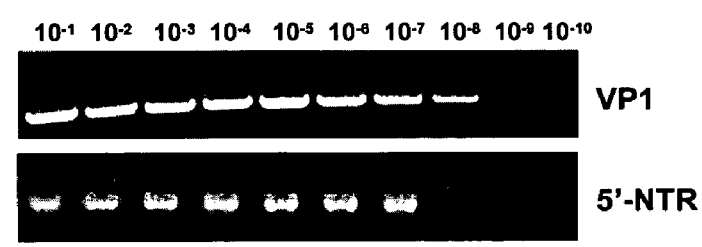

The sensitivity of the VP1 RT-snPCR assay was also compared to that of a 5'NTR RT-snPCR assay (Nix et al., Neurol. 62:1372-77, 2004) by serially diluting RNA extracted from a recent EV68 clinical isolate and running both the VP1 and 5'NTR RT-snPCR assays in parallel using the same diluted RNA preparations. The diluted EV68 clinical isolate RNA was amplified from the $10^{-1}$-$10^{-7}$ dilutions with the 5'NTR RT-snPCR assay, and from the $10^{-1}$-$10^{-8}$ dilutions with the VP1 RT-snPCR assay (FIG. 3C).

Example 4

Application to Clinical Specimens

This example demonstrates the application of methods of using specific primers to amplify and identify enteroviruses from clinical specimens.

To demonstrate the clinical application of the VP1 RT-snPCR method, RNA was extracted from original clinical specimens obtained from patients with a number of different enteroviral illnesses. The specimens and associated illnesses included cerebrospinal fluid (aseptic meningitis), stool (aseptic meningitis), rectal swab (febrile rash), nasopharyngeal swab (mild upper respiratory illness), conjunctival swab (acute hemorrhagic conjunctivitis), serum (febrile rash), and postmortem liver tissue (neonatal sepsis-like illness).

Stool suspensions were prepared by adding 5 ml of phosphate-buffered saline, 1 g of glass beads (Corning Inc., Corning, N.Y.), and 0.5 ml of chloroform to 1 g of stool, shaking the mixture vigorously for 20 min in a mechanical shaker, and centrifugation at 1500 g for 20 min at 4° C. (World Health Organization, Manual for the virological investigation of polio, World Health Organization, Geneva, 2001). For rectal swab samples, the fluid was centrifuged at 13,000 g for 1 min at room temperature to remove solids, and the supernatant was transferred to a fresh tube. For fecal specimens (stool suspensions or clarified rectal swab supernatants), 140 µl of the specimen extract was combined with an equal volume of Vertrel XF (Miller-Stephenson Chemical Co., Danbury, Conn.), shaken vigorously, and then centrifuged at 13,000 g for 1 min at room temperature. The aqueous phase was transferred to a fresh tube. Other specimen types, including cerebrospinal fluid, virus isolates, and supernatants from nasopharyngeal, oropharyngeal, and conjunctival swab samples, were processed without pretreatment. Twenty micrograms of proteinase K (Roche Applied Science, Indianapolis, Ind.) was added to 140 µl of each liquid specimen or fecal extract, and then incubated for 30 min at 37° C. Nucleic acid was extracted from the digested specimen with the QIAamp Viral RNA Mini Kit (Qiagen, Inc., Valencia, Calif.), which was used according to the manufacturer's instructions. Eluted RNAs were dried passively in a bench top desiccator under vacuum. The dried RNA was resuspended in 16 µl of sterile nuclease-free water and stored at −20° C. until use. Synthesis of cDNA and RT-PCR amplification were carried out as described herein in Example 2.

Figure 4:
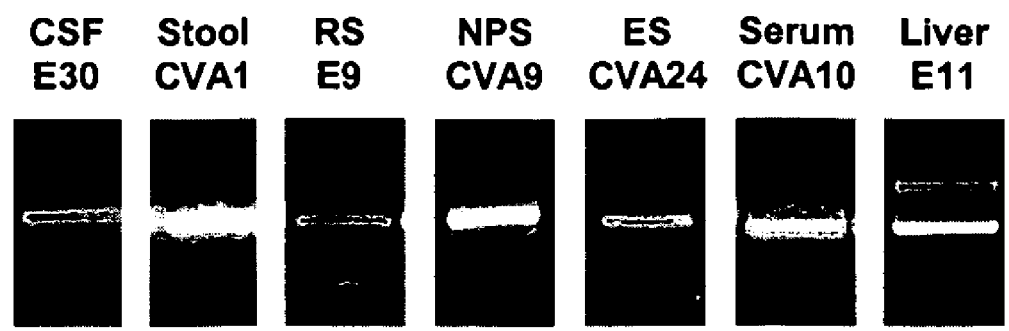
FIG. 4 illustrates the amplification of RNA extracted directly from original clinical specimens using VP1 RT-snPCR. For each reaction, 50 µl of each semi-nested PCR2 product was analyzed and gel purified by electrophoresis on a 1.5% agarose gel, containing 0.5 micrograms ethidium bromide per milliliter. The specimens tested were cerebrospinal fluid (CSF), stool, rectal swab (RS), nasopharyngeal swab (NPS), eye (conjunctival) swab (ES), serum, and postmortem liver tissue.

From each of these RNA templates, a specific product was amplified by VP1 RT-snPCR (FIG. 4). In each assay, the tested RNA represents the equivalent of approximately 45 µl of original specimen fluid or 10 µg of stool. Following gel purification, the EV present in each specimen was identified by amplicon sequencing and comparison to a database of EV VP1 sequences. All of the amplification products yielded clean, readable sequences, including those with weak or multiple bands (for example, rectal swab and liver). The identified EVs were E30 (cerebrospinal fluid), CVA1 (stool), E9 (rectal swab), CVA9 (nasopharyngeal swab), CVA24 (conjunctival swab), CVA10 (serum), and E11 (liver).

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. A method of detecting an enterovirus (EV) RNA sequence in a sample, comprising:

contacting the sample with one or more nucleic acid cDNA primers comprising a sequence as set forth in any one of SEQ ID NOs: 1-4, that hybridize to an EV VP1 encoding sequence;

reverse transcribing EV cDNA from the EV RNA sequence;

amplifying at least a portion of the EV cDNA using a first nucleic acid primer pair, wherein the first forward primer comprises a sequence as set forth in SEQ ID NO: 5 and hybridizes to an EV VP3 encoding sequence, and the first reverse primer comprises a sequence as set forth in SEQ ID NO: 6 and hybridizes to an EV VP1 encoding sequence, thereby generating an EV amplicon;

amplifying at least a portion of the EV amplicon using a second nucleic acid primer pair, wherein the second forward primer comprises a sequence as set forth in SEQ ID NO: 11 or SEQ ID NO: 13, and the second reverse primer comprises a sequence as set forth in SEQ ID NO: 12 or SEQ ID NO: 14, wherein both the second forward and reverse primers hybridize to an EV VP1 encoding sequence; and determining whether an amplified EV amplicon is present, thereby detecting an EV nucleic acid sequence in the sample.

2. The method of claim 1, wherein the amplification comprises a polymerase chain reaction amplification.

3. The method of claim 1, wherein determining whether an amplified EV amplicon is present comprises:

gel electrophoresis and visualization of the amplified EV amplicon;

capillary electrophoresis and detection of the amplified EV amplicon; or hybridization of a labeled probe to the amplified EV amplicon.

4. The method of claim 1, wherein the EV RNA is extracted from the sample.

5. The method of claim 1, further comprising electrophoresing and sequencing at least a portion of the amplified EV amplicon, and wherein the method of detecting an EV RNA sequence in a sample comprises a method of identifying the EV in the sample.

6. The method of claim 1, wherein the second forward primer comprises a sequence as set forth in SEQ ID NO: 11, and the second reverse primer comprises a sequence as set forth in SEQ ID NO: 12.

7. A method of detecting an enterovirus (EV) RNA sequence in a sample, comprising:

contacting the sample with one or more nucleic acid cDNA primers that hybridize to an EV VP1 encoding sequence;

reverse transcribing EV cDNA from the EV RNA sequence;

amplifying at least a portion of the EV cDNA using a first nucleic acid primer pair, wherein the first forward primer hybridizes to an EV VP3 encoding sequence and the first reverse primer hybridizes to an EV VP1 encoding sequence, thereby generating an EV amplicon;

amplifying at least a portion of the EV amplicon using a second nucleic acid primer pair, wherein the second forward primer comprises a sequence as set forth in SEQ ID NO: 13 and the second reverse primer comprises a sequence as set forth in SEQ ID NO:12 or SEQ ID NO:14, and both second primers hybridize to an EV VP1 encoding sequence; and determining whether an amplified EV amplicon is present, thereby detecting an EV nucleic acid sequence in the sample.

8. The method of claim 7, wherein the one or more nucleic acid cDNA primers comprise a sequence as set forth in any one of SEQ ID NOs: 1-4, the first forward primer comprises a sequence as set forth in SEQ ID NO: 5, the first reverse primer comprises a sequence as set forth in SEQ ID NO: 6.

9. The method of claim 8, wherein the second reverse primer comprises a sequence as set forth in SEQ ID NO: 14.

10. A method of detecting an enterovirus (EV) RNA sequence in a sample, comprising:

contacting the sample with one or more nucleic acid cDNA primers that hybridize to an EV VP1 encoding sequence;

reverse transcribing EV cDNA from the EV RNA sequence;

amplifying at least a portion of the EV cDNA using a first nucleic acid primer pair, wherein the first forward primer hybridizes to an EV VP3 encoding sequence and the first reverse primer hybridizes to an EV VP1 encoding sequence, thereby generating an EV amplicon;

amplifying at least a portion of the EV amplicon using a second nucleic acid primer pair, wherein the second forward primer comprises a sequence as set forth in SEQ ID NO:11 or SEQ ID NO:13 and the second reverse primer comprises a sequence as set forth in SEQ ID NO:14, and both second primers hybridize to an EV VP1 encoding sequence; and determining whether an amplified EV amplicon is present, thereby detecting an EV nucleic acid sequence in the sample.

11. The method of claim 10, wherein the one or more nucleic acid cDNA primers comprise a sequence as set forth in any one of SEQ ID NOs: 1-4, the first forward primer comprises a sequence as set forth in SEQ ID NO: 5, the first reverse primer comprises a sequence as set forth in SEQ ID NO: 6.

* * * * *